US009964534B2

(12) United States Patent
Laughlin, II et al.

(10) Patent No.: US 9,964,534 B2
(45) Date of Patent: May 8, 2018

(54) METHOD OF MAKING A SKIN CARE COMPOSITION

(71) Applicant: The Procter & Gamble Company, Cincinnati, OH (US)

(72) Inventors: Leo Timothy Laughlin, II, Mason, OH (US); Tomohiro Hakozaki, Cincinnati, OH (US); Wenzhu Zhao, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days. days.

(21) Appl. No.: 14/847,042

(22) Filed: Sep. 8, 2015

(65) Prior Publication Data

US 2016/0077080 A1    Mar. 17, 2016

Related U.S. Application Data

(60) Provisional application No. 62/050,008, filed on Sep. 12, 2014.

(51) Int. Cl.
| | |
|---|---|
| C12Q 1/68 | (2006.01) |
| G01N 33/50 | (2006.01) |
| A61K 8/365 | (2006.01) |
| A61Q 19/02 | (2006.01) |
| G01N 33/68 | (2006.01) |

(52) U.S. Cl.
CPC ........... G01N 33/502 (2013.01); A61K 8/365 (2013.01); A61Q 19/02 (2013.01); C12Q 1/6813 (2013.01); C12Q 1/6876 (2013.01); C12Q 1/6881 (2013.01); G01N 33/5008 (2013.01); G01N 33/5023 (2013.01); G01N 33/5026 (2013.01); G01N 33/6875 (2013.01); *C12Q 2600/136* (2013.01); *C12Q 2600/158* (2013.01); *G01N 2333/4706* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | |
|---|---|---|
| 2002/0034772 A1 | 3/2002 | Orlow |
| 2007/0042064 A1 | 2/2007 | Leverett |
| 2008/0206373 A1 | 8/2008 | Millikin |
| 2010/0040608 A1 | 2/2010 | Wahren-Herlenius |
| 2011/0003747 A1* | 1/2011 | Coloumbe ............. A61K 31/00 514/9.2 |
| 2011/0262551 A1* | 10/2011 | Nizard .................. A61Q 19/08 424/537 |
| 2013/0261007 A1 | 10/2013 | Hakozaki |
| 2016/0077082 A1 | 3/2016 | Laughlin, II et al. |

FOREIGN PATENT DOCUMENTS

| | | |
|---|---|---|
| EP | 2746253 A1 | 6/2014 |
| JP | 2012201649 A | 10/2012 |
| WO | WO2008073684 A1 | 6/2008 |
| WO | WO 2009/1344 B4 | 1/2009 |
| WO | WO2009134404 A2 | 11/2009 |
| WO | WO2012011904 A1 | 1/2012 |

OTHER PUBLICATIONS

Bumgarner et al. Current Protocols in Molecular Biology. Jan. 2013. 22.1.1-22.1.11.*
International Search Report PCT/US2015/048819; dated Dec. 1, 2015; 13 pages.
R. Osborne et al: "Application of 1-13 genomics to breakthroughs in the cosmetic treatment of skin ageing and discoloration". British Journal of Dermatology. vol. 166. Jun. 7, 2012 (Jun. 7, 2012) pp. 16-19.
Orang et al., Mechanisms of miRNA-Mediated Gene Regulation from Common Downregulation to mRNA-Specific Upregulation, International Journal of Genomics, vol. 2014, 16 pages.
Hydrolyzed *Prunus Domestica* (Plum) Clairju Natural Cosmetic Ingredient, Retrieved from Internet on Nov. 12, 2015: URL: http://www.21food.com/showroom/1704659/product/hydrolyzed-prunus-domestica-(plum)-clairju-natural-cosmetic-ingredient.html.
International Search Report and Written Opinion of the International Searching Authority, PCT/US2015/048825, dated Dec. 14, 2015, 16 pages.
Kubo et al., Methyl p-coumarate, a melanin formation inhibitor in B16 mouse melanoma cells, Bioorganic & Medicinal Chemistry, vol. 12 (2004), pp. 5349-5354.

* cited by examiner

*Primary Examiner* — Joseph G Dauner
(74) *Attorney, Agent, or Firm* — John G. Powell

(57) ABSTRACT

A method of making a skin composition that includes an effective amount of skin care agent selected to inhibit HMGB1 stimulation of human melanocytes. The method includes determining the level of high-mobility group protein B1 (HMGB1), messenger RNA associated with the expression and/or regulation of HMGB1 (HMGB1 mRNA), and/or micro-RNA associated with the expression and/or regulation of HMGB1 (HMGB1 miRNA) present in the test sample, and identifying the test agent as a skin tone agent when there is no increase in HMGB1 level, a downregulation in transcription of HMGB1 mRNA, and/or an upregulation of HMGB1 miRNA. The method also includes identifying a test agent as a skin tone agent when the test agent inhibits or prevents an increase in melanocyte dendricity and/or body size caused by HMGB1, and incorporating the skin tone agent in a dermatologically acceptable carrier.

10 Claims, 3 Drawing Sheets

```
SEQUENCE LISTING

<160> NUMBER OF SEQ ID NOS: 16

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110
```

```
Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Asp Glu Glu Asp Glu Asp Glu
    195                 200                 205

Glu Glu Asp Asp Asp Asp Glu
    210                 215

<210> SEQ ID NO 2
<211> LENGTH: 22
<212> TYPE: RNA
<213> ORGANISM: Homo sapiens

<400> SEQUENCE: 2
ugagguagua gguugugugg uu                                                    22

<210> SEQ ID NO 3
<211> LENGTH: 22
<212> TYPE: DNA
<213> ORGANISM: Homo sapiens

<400> SEQUENCE: 3
ugagguagga gguuguauag uu                                                    22

<210> SEQ ID NO 4
<211> LENGTH: 22
<212> TYPE: RNA
<213> ORGANISM: Homo sapiens

<400> SEQUENCE: 4
ugagguagua guuuguacag uu                                                    22

<210> SEQ ID NO 5
<211> LENGTH: 22
<212> TYPE: RNA
<213> ORGANISM: Homo sapiens

<400> SEQUENCE: 5
aacccguaga uccgaacuug ug                                                    22

<210> SEQ ID NO 6
<211> LENGTH: 22
<212> TYPE: RNA
<213> ORGANISM: Homo sapiens

<400> SEQUENCE: 6
ucagugcacu acagaacuuu gu                                                    22

<210> SEQ ID NO 7
<211> LENGTH: 22
<212> TYPE: RNA
<213> ORGANISM: Homo sapiens

<400> SEQUENCE: 7
```

```
ucagugcauc acagaacuuu gu                                              22

<210> SEQ ID NO 8
<211> LENGTH: 23
<212> TYPE: RNA
<213> ORGANISM: Homo sapiens

<400> SEQUENCE: 8
aacauucauu guugucggug ggu                                             23

<210> SEQ ID NO 9
<211> LENGTH: 23
<212> TYPE: RNA
<213> ORGANISM: Homo sapiens

<400> SEQUENCE: 9
acugcccuaa gugcuccuuc ugg                                             23

<210> SEQ ID NO 10
<211> LENGTH: 22
<212> TYPE: RNA
<213> ORGANISM: Homo sapiens

<400> SEQUENCE: 10
aacuggcccu caaagucccg cu                                              22

<210> SEQ ID NO 11
<211> LENGTH: 22
<212> TYPE: RNA
<213> ORGANISM: Homo sapiens

<400> SEQUENCE: 11
aagcugccag uugaagaacu gu                                              22

<210> SEQ ID NO 12
<211> LENGTH: 21
<212> TYPE: RNA
<213> ORGANISM: Homo sapiens

<400> SEQUENCE: 12
uucaaguaau ucaggauagg u                                               21

<210> SEQ ID NO 13
<211> LENGTH: 22
<212> TYPE: RNA
<213> ORGANISM: Homo sapiens

<400> SEQUENCE: 13
cuggcccucu cugcccuucc gu                                              22

<210> SEQ ID NO 14
<211> LENGTH: 21
<212> TYPE: RNA
<213> ORGANISM: Homo sapiens

<400> SEQUENCE: 14
aauggcgcca cuaggguugu g                                               21

<210> SEQ ID NO 15
<211> LENGTH: 21
<212> TYPE: RNA
<213> ORGANISM: Homo sapiens

<400> SEQUENCE: 15
```

```
uccucuucuc ccuccuccca g                                           21

<210> SEQ ID NO 16
<211> LENGTH: 22
<212> TYPE: RNA
<213> ORGANISM: Homo sapiens

<400> SEQUENCE: 16
uauugcacuu gucccggccu gu                                          22
```

METHOD OF MAKING A SKIN CARE COMPOSITION

FIELD

The present disclosure relates to methods of identifying skin care actives that boost inhibition of HMGB1 activation of melanocytes, compositions containing such actives, and methods of making such compositions.

BACKGROUND

Melanin is fundamental compound in skin pigmentation, and much of the skin pigmentation observed is dependent upon the loading and retention of melanosomes in the keratinocytes. Melanin is produced by a complex set of reactions within a melanocyte involving, at a basic level, the enzyme tyrosinase and L-tyrosine as a substrate. Melanogenesis can be stimulated by paracrine factors originating from keratinocytes such as stem cell factor and endothelin-1 in response to UV stress. During melanogenesis, tyrosinase catalyzes the conversion of L-tyrosine to DOPA (L-3,4-dihydroxyphenylalanine) and of DOPA to dopaquinone. Dopaquinone undergoes further conversion to form melanin. Melanin aggregates in organelles known as the melanosomes which are transferred to keratinocytes along slender filaments of the melanocyte known as dendrites. Since there are approximately 36 keratinocytes for each melanocyte in the epidermis, the melanocytes rely on these dendritic structures to "reach" neighboring keratinocytes for melanosome transfer. Melanin carrying keratinocytes then migrate upward toward the skin surface in a constant renewal process.

There are approximately 1500 gene products expressed in a melanosome, with 600 of them being expressed at any given time, and 100 of them believed to be unique to the melanosome. In addition, there are many regulatory elements involved in signaling, in the transport of melanosomes within the melanocyte, and in the transfer of melanosomes to the keratinocytes. Some pathways are relatively well elucidated, while others are not. Identifying and better understanding the biochemical pathways involved in melanin transfer can help identify skin tone agents for regulating hyperpigmentation and melanin overproduction.

Accordingly, it would be desirable to identify skin care actives that inhibit the transfer of melanin from melanocytes to keratinocyes. It would also be desirable to formulate cosmetic compositions for improving the appearance of hyperpigmented skin that include such actives. It would further be desirable to treat skin pigmentation conditions using such compositions.

SUMMARY

Disclosed herein is a method of making a skin care composition. The screening method comprises suspending cells in a first medium at a concentration of between about 1,000 cells/mL and about 2,000,000 cells/mL to provide a test suspension; placing at least some of the test suspension in a container; contacting at least some of the suspended cells in the container with a test agent to provide a test sample; determining a level of high-mobility group protein B1 (HMGB1), messenger RNA associated with the expression and/or regulation of HMGB1 (HMGB1 mRNA), and/or micro-RNA associated with the expression and/or regulation of HMGB1 (HMGB1 miRNA) present in the test sample; comparing the level of HMGB1, HMGB1 mRNA and HMGB1 miRNA present in the test sample to a control; identifying the test agent as a skin tone agent when the level of HMGB1 present in the test sample does not correspond to an increase in HMGB1 level, the level of HMGB1 mRNA corresponds to a downregulation in transcription of HMGB1 mRNA, and/or the level of HMGB1 miRNA corresponds to an upregulation of HMGB1 miRNA; and incorporating the test agent into a skin care composition. In some instances, the method herein may include one or more of the following features, in any combination: cells selected from the group consisting of keratinocytes, fibroblasts, and macrophages, optionally suspended in a medium; removing the optional medium, when included, prior to contacting the cells with the test agent; diluting the test agent in a medium, which may be the same or different from the medium in the test suspension; chemically lysing the cells in the test sample; determining total protein level of the test sample and normalizing the level of HMGB1 present in the test sample against the total protein level; isolating, labeling, and hybridizing HMGB1 mRNA or HMGB1 miRNA is to a microarray; diluting the test agent to a concentration of from 0.0001% to 10% w/v; including a solublizer such as dimethyl sulfoxide in the control.

Also disclosed in a method of improving the appearance of a hyperpigmented spot, comprising: identifying a target portion of skin comprising a hyperpigmented spot; and applying one of the compositions herein the target portion of skin for an amount of time sufficient for the skin tone agent to improve the appearance of the hyperpigmented spot by inhibiting HMGB1 stimulation of melanocytes that are present in the target portion of skin. In some instances, the improvement in appearance corresponds to at least one of a reduction in size of the hyperpigmented spot, a lightening of the hyperpigmented spot, or a decrease in the amount of melanin of the hyperpigmented spot.

Further disclosed is a screening method for identifying a test agent as a skin tone agent, comprising suspending melanocytes in a first medium at a concentration of between about 1,000 cells/mL and about 1,000,000 cells/mL to provide a test suspension. At least some of the test suspension is placed in a container; and at least some of the suspended melanocytes in the container are contacted with HMGB1 followed by contact with a test agent. Dendricity and/or cell body size of the melanocytes in the test sample is determined and compared to a control. The test agent is identified as a skin tone agent when the measured dendricity and/or cell body size does not correspond to at least one of an increase in dendricity and cell body size.

DETAILED DESCRIPTION

Figure 1:
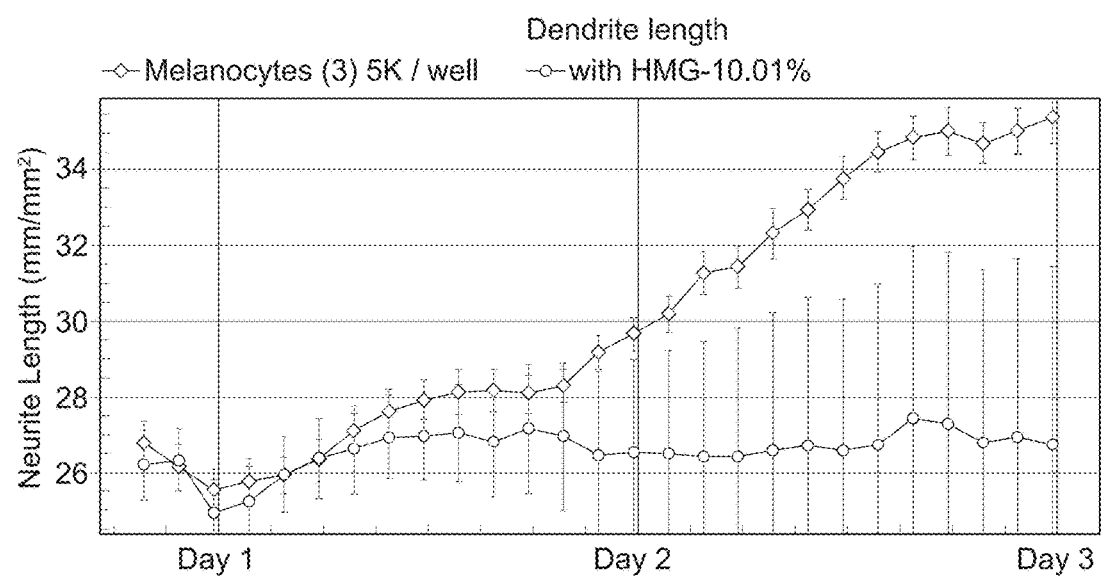
FIG. 1 is a chart illustrating the increase in dendricity of a melanocyte contacted with HMGB1.

The terminology used in the description herein is for describing particular examples only and is not intended to be limiting. As used in the description and the appended claims, the singular forms "a," "an," and "the" are intended to include the plural forms as well, unless the context clearly indicates otherwise. All percentages are by weight of the composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. All measurements made are at 25° C., unless otherwise designated. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

Sequence Listing

A sequence listing that sets forth the amino acid or nucleotide sequence for SEQ ID NO: 1 to 16 is being filed concurrently with the present application as an ASCII text file titled "13534M2_seq_list_ST25." This ASCII text file was created on Sep. 8, 2015 and is 4.24 KB in size. In accordance with MPEP §605.08 and 37 CFR §1.52(e), the subject matter in the ASCII text file is incorporated herein by reference.

Definitions

"Age spot" means a hyperpigmented spot caused by intrinsic or extrinsic aging factors.

"Apply" or "application", as used in reference to a composition, means to apply or spread the compositions of the present invention onto a human skin surface such as the epidermis.

"Dendricity" means the total length of dendrites measured according to the method herein. Dendricity may be measured with an Incucyte ZOOM® live cell imaging system available from Essen Bioscience, Ann Arbor, Mich.

"Dendrite" means branched projections of a melanocyte that act to transfer melanosomes from the melanocyte cell body to adjacent keratinocytes.

"Derivative" means a molecule similar to that of another one, but differing from it in respect of a certain functional moiety. Suitable functional moieties include esters, ethers, amides, amines, carboxylic acids, hydroxyls, halogens, thiols, and/or salt derivatives of the relevant molecule.

"Dermatologically acceptable" means that the compositions or components described are suitable for use in contact with human skin tissue without undue toxicity, incompatibility, instability, allergic response, and the like.

"Hyperpigmented spot" means a defined area of skin wherein the pigmentation is greater than that of an adjacent area of skin due to localized and chronic or systemic overproduction of melanin. Hyperpigmented spots typically are between about 2 mm and about 10 mm in diameter but smaller or larger spots are possible. Hyperpigmented spots can include one or more of age spots, sun spots, solar lentigos, hypo-melanotic lesions, freckles, and melasma spots.

"Facial skin surfaces" means one or more of forehead, periorbital, cheek, perioral, chin, and nose skin surfaces.

"RNA" means ribonucleic acid.

"Safe and effective amount" means an amount of a compound or composition sufficient to significantly induce a desired benefit, but low enough to avoid serious side effects (i.e., to provide a reasonable benefit to risk ratio), within the scope of sound judgment of the skilled artisan).

"Skin" means the outermost protective covering of mammals that is composed of cells such as keratinocytes, fibroblasts and melanocytes. Skin includes an outer epidermal layer and an underlying dermal layer. Skin may also include hair and nails as well as other types of cells commonly associated with skin, such as, for example, myocytes, Merkel cells, Langerhans cells, macrophages, stem cells, sebocytes, nerve cells and adipocytes.

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturisation of the skin, improving the appearance of fine lines and/or wrinkles, improving skin exfoliation or desquamation, plumping the skin, improving skin bather properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity; improve skin hydration; improve skin condition; and improve cell metabolism).

"Skin care composition" means a composition that includes a skin care active and regulates and/or improves a skin condition.

"Skin tone agent" means a skin care active that regulates melanin production signals, synthesis of melanin, and transfer of melanin between the melanocyte and a keratinocyte, and/or melanin degradation within a keratinocyte. Skin tone agents can improve the appearance of uneven skin tone and hyperpigmented spots by acting as a skin lightening or pigmentation reducing cosmetic agent.

"Skin tone" means the overall appearance of melanin in the skin caused by the systemic, rather than transient, synthesis of melanin. Skin tone is typically characterized over a larger area of the skin. The area ideally may be less than 100 mm$^2$, but larger areas are envisioned such as the entirety of the facial skin or other bodily skin surfaces (e.g., arms, legs, back, hands, neck, chest and abdomen). Skin tone can be measured by image analysis. For example, overall lightness can be measured using the L* coordinate in the L*a*b* color space (International Commission on Illumination). Chromophore mapping such as melanin mapping and melanin concentration may be used as an indicator of overall skin tone. Mean melanin may be calculated from the chromophore map data. Additionally, skin tone evenness can be determined by melanin evenness which also may be calculated from the chromophore map data. Suitable chromophore mapping techniques are discussed in the example below.

Skin pigmentation is a process involving the production of melanin in melanocytes at the basal epidermal layer. Much of the skin pigmentation observed in a person is dependent upon the loading and retention of melanosomes in keratinocytes, which is driven by a complex set of biochemical processes that have not been fully elucidated. It has now been surprisingly discovered that high-mobility group protein B1, represented by SEQ ID No. 1 ("HMGB1") stimulates dendricity and cell body area growth in primary human melanocytes without enhancing melanocyte proliferation. This finding directly implicates HMGB1 in skin pigmentation by stimulation of shipping infrastructure required to facilitate transfer of melanosomes from melanocytes to keratinocytes.

HMGB1 is known for its role as a chromatin protein, and is also known to function as a ligand for the Receptor for Advanced Glycation Endproducts ("RAGE") and certain toll like receptors ("TLRs"). HMGB1 is further known to be released from keratinocytes after UVB exposure relative to its role in neutrophil infiltration during inflammation, and was thought to perhaps play an indirect role in skin pigmentation via an inflammation pathway. However, prior to the present discovery, HMGB1 was not known to play a role in melanosome transfer, and thus play a direct role in skin pigmentation. As a result, it may be possible to improve the appearance of hyperpigmented spot and/or uneven skin tone by inhibiting the activity of the HMGB1 and/or down-regulating the expression of HMGB1 in a target area of skin.

FIG. 1 illustrates an increase in dendricity of a melanocyte contacted with HMGB1 (recombinant HIS-tagged HMGB1 available from Sigma). As shown in FIG. 1, the melanocytes treated with the HMGB1 have significantly longer dendrites relative to the control over the span of three days. The test sample and control used in FIG. 1 were prepared and analyzed according to the methods herein.

Figure 2:
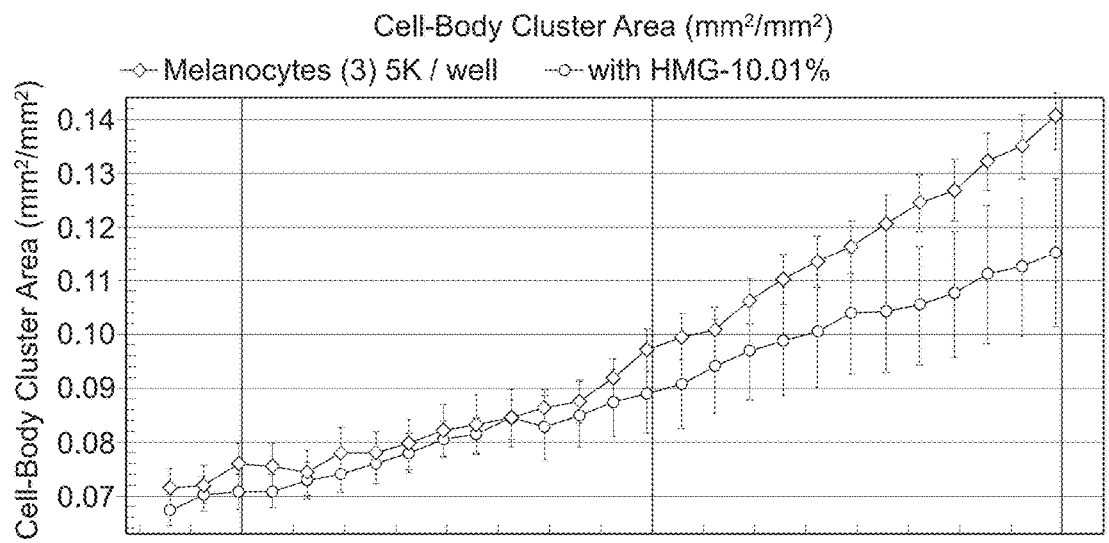
FIG. 2 is a chart illustrating the increase in cell body size of a melanocyte contacted with HMGB1.

FIG. 2 illustrates an increase in cell body size of a melanocyte contacted with HMGB1 (recombinant HIS-tagged HMGB1 available from Sigma). As shown in FIG. 2, the melanocytes treated with the HMGB1 have a significantly larger cell body size relative to the control over the span of three days. The test sample and control used in FIG. 1 were prepared and analyzed according the methods herein.

Figure 3:
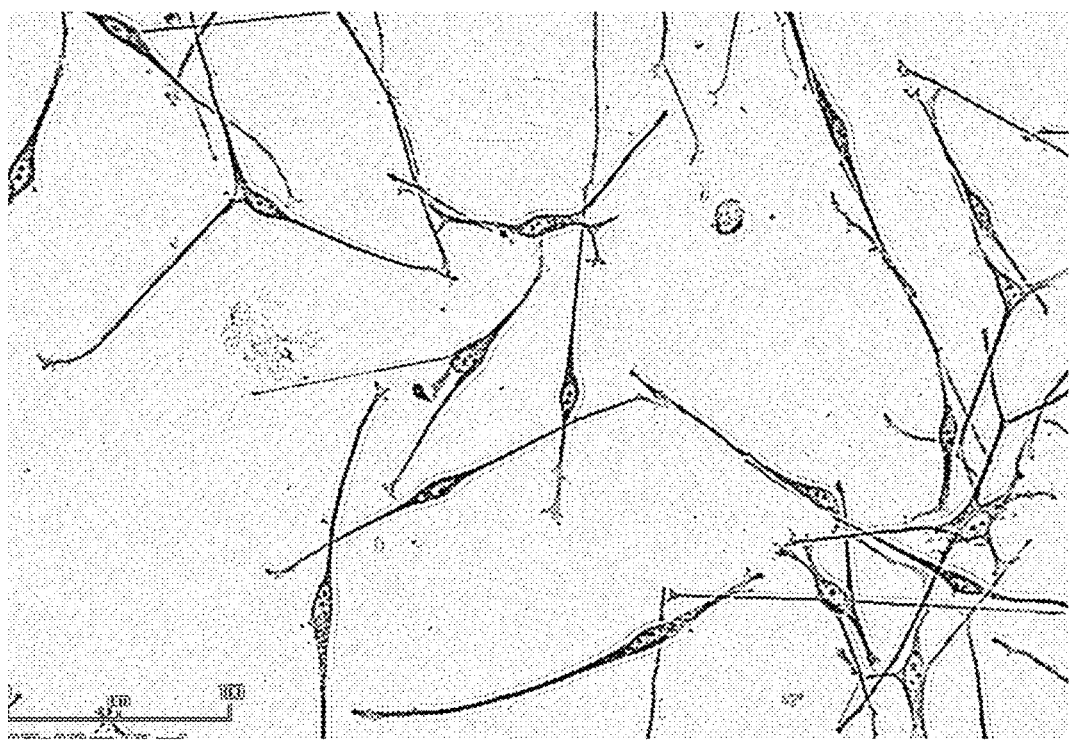
FIG. 3 is a micrograph of melanocytes before treatment with HMGB1.
Figure 4:
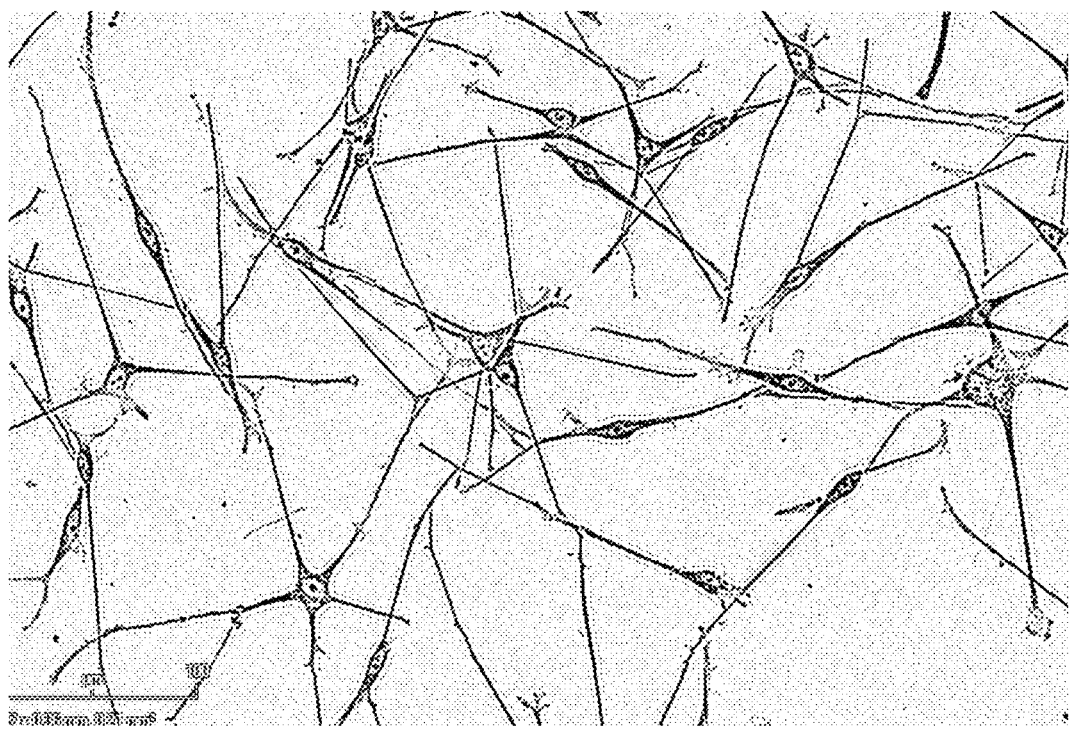
FIG. 4 is a micrograph of melanocytes after treatment with HMGB1.

FIGS. 3 and 4 are micrographs of melanocytes before and after (respectively) treatment with HMGB1. As can be seen in FIGS. 3 and 4, the melanoctyes treated with HMGB1 exhibit increased dendricity and cell body size.

Method of Identifying Skin Tone Agents

The surprising discovery that HMGB1 stimulates dendricity and cell body area growth in primary human melanocytes without enhancing melanocyte proliferation has led to the creation of new methods of identifying skin tone agents. The present methods provide a convenient means for an in vitro screening assay for identifying test agents and combinations of test agents as potential skin tone agents, based on the ability of the test agent to regulate HMGB1 level and/or activity in the assay. Test agents to be evaluated according to the present methods may be selected by any suitable means known in the art. For example, connectivity mapping may be used to identify test agents that are known to modulate a particular gene or set of genes associated with a gene expression signature, biological process, pathway or theme of interest. A nonlimiting example of using connectivity mapping to identify potential skin tone agents is disclosed in US Publication No. 20130261007A1, filed by Hakozaki, et al., on Mar. 27, 2013.

Once a test agent or combination of test agents is selected, a sample of cells is contacted with the test agent(s). Cells suitable for use with the present methods are not particularly limited as long as they are capable of producing HMGB1 (e.g., skin cells such as keratinocytes and fibroblasts are particularly suitable). The cells may be harvested from donors and/or purchased from vendors who sell commercially available cell lines. The cells may be cultured in a suitable medium (e.g., EpiLife® available from Life Technologies) and/or incubated prior to creation of the test sample (e.g., from 1 hour to 2 weeks). Test samples comprising the cells, optionally suspended or adhered in a suitable medium, the test agent(s) and other necessary or optional ingredients are provided in a suitable container (e.g., 12-well plate). Each test sample should include enough cells to provide a suitable level of sensitivity for detection of the biomarker being measured (e.g., at least 1,000 cells/mL, but typically less than 2,000,000 cells/mL). The cells, test agent(s) and other ingredients may be added to the container in any order, as desired. For example, a test sample may be formed by placing a multitude of cells in a suitable container and then adding a test agent. In another example, a test sample may be prepared by placing a test agent, and optionally other ingredients, in a suitable container, and adding the cells, and optionally other ingredients, to the container. In some instances, the test sample may include cells without a suspension medium. For example, the suspension medium may be removed after placing the suspended cells in the container. In some instances, the test agent may be incorporated into a solution such as, for example, a suitable cell suspension medium at a dilution of a 1:1000, and then added to the test sample. The test sample may be subjected to any conventional storage, culturing or other sample preparation techniques known to be used when measuring the particular properties described herein.

In some instances, the present methods may use a control sample. The control sample may be prepared in substantially the same way as the test sample, except without the test agent. Alternatively, the control may include a different suspension medium and/or type of cell. The selected indicator (e.g., biomarker level, dendricity or cell body size) may be measured in the control sample in substantially the same way as the test sample, but need not necessarily be so. Various positive and/or negative controls that are known for ensuring the viability and/or responsiveness of the cells to stimuli are also contemplated for use herein.

Suspension media, which are optionally used in the storage, preparation and/or processing of the cells, test agents and/or test samples of the present methods, are typically aqueous solutions. Thus, when an aqueous suspension medium is included in the test sample and a water insoluble test agent is tested, it may be desirable to include a suitable solublizer in the test sample and/or in the dosing sample (i.e., the solution containing the test agent) to solublize the test agent. When testing multiple test agents that have different solubility (e.g., water soluble and water insoluble), it would be desirable to use a single control. By including one or more solublizers in the control, the same control can be used for both the water soluble and water insoluble test agents. Solublizer(s) that do not affect the particular properties being measured in the test are preferred. A nonlimiting example of a suitable solublizer is dimethyl sulfoxide ("DMSO").

To complete preparation of the test sample, the cells are contacted with the test agent, and optionally other ingredients. The test sample is then analyzed for the particular indicator of interest (e.g., biomarker level, dendricity, and/or cell body size). It may be desirable to wait at least one hour up to 48 hours (e.g., 1, 2, 3, 4, 5, 6, 7, 8, 9, 10, 11, 12, 13, 14, 15, 16, 17, 18, 19, 20, 21, 22, 23, or even 24 hours) after contacting the cells in the test sample with the test agent to measure the indicator. It may be desirable to measure the indicator of interest hourly, or at any other desired periodicity, to determine the amount and/or rate of change in the indicator of interest at a particular time (e.g., 6, 12, 24 or 48 hours after contacting the cells with the test agent). The time required for an agent to detectably modify an indicator may vary based on the test agent selected. Thus, it is important to monitor the activity of the test agent, and select the appropriate time to determine whether the test agent is identified as a skin tone agent.

In some instances, the indicator of interest is one or more biomarkers. Some nonlimiting examples of biomarkers of interest include HMGB1 level, levels of messenger RNA ("mRNA") associated with the expression and/or regulation of HMGB1, and levels of micro-RNA ("miRNA") associated with the expression and/or regulation of HMGB1. The level of the selected biomarker(s) measured in the test sample is compared to a control to determine whether there is an indication that the test agent affected the expression and/or regulation of the biomarker. In some instances, the biomarker of interest may be isolated from the supernatant of the test sample. Additionally or alternatively, the biomarker may be isolated from the cells themselves, for example, by lysing the cells. It may be desirable to use a detergent or other chemical means to lyse the cells to reduce the variability associated with mechanical lysing techniques and the long testing time of freeze-thaw lysing techniques. A biomarker of interest and/or total protein content may be determined from the lysed cells, for example, using a bicinchoninic acid ("BCA") protein assay (i.e., HMGB1 level or total protein) or labeling mRNA and/or miRNA and hybridizing it to a suitable microarray. When HMGB1 level is the biomarker of interest, the test agent is identified as a skin tone agent when the measured HMGB1 level "does not correspond to an increase in HMGB1 level," which means that (i) the HMGB1 level of the test sample did not increase relative to a control; (ii) the HMGB1 level of the test sample increased, but less than the HMGB1 level of the control; or (iii) the HMGB1 level of the test sample increased, but the average rate of increase in HMGB1 level of the test sample was less than the average rate of increase in HMGB1 level of the control. When mRNA encoded by the HMGB1 gene ("HMGB1 mRNA") is the biomarker of interest, the test agent is identified as a skin tone agent when "HMGB1 mRNA transcription is downregulated," which means that (i) HMGB1 mRNA level decreased relative to the control; (ii) HMGB1 mRNA level of the test sample increased, but less than HMGB1 mRNA level of the control; or (iii) the HMGB1 mRNA level of the test sample increased, but the average rate of increase in HMGB1 mRNA level of the test sample was less than the average rate of increase in HMGB1 mRNA level of the control. If miRNA associated with the post-transcriptional regulation of HMGB1 gene expression ("HMGB1 miRNA"), for example via RNA silencing, is the biomarker of interest, then the test agent is identified as a skin tone agent "when HMGB1 miRNA is upregulated," which means that (i) the HMGB1 miRNA level of the test sample increased relative to a control; (ii) the HMGB1 miRNA level of the test sample decreased, but less than the HMGB1 miRNA level of the control decreased; or (iii) the HMGB1 miRNA level of the test sample decreased, but the average rate of decrease in HMGB1 miRNA level of the test sample was less than the average rate of decrease in HMGB1 miRNA level of the control.

Some non-limiting examples of miRNA for use as a biomarker of interest herein are hsa-let-7b-5p, hsa-let-7e-5p, hsa-let-7g-5p, hsa-miR-100-5p, hsa-miR-148a-3p, hsa-miR-148b-3p, hsa-miR-181d-5p, hsa-miR-18a-3p, hsa-miR-193b-3p, hsa-miR-22-3p, hsa-miR-26b-5p, hsa-miR-328-3p, hsa-miR-652-3p, hsa-miR-877-3p, hsa-miR-92a-3p, represented by SEQ ID Nos. 2 to 16, respectively. These miRNA are believed to regulate HMGB1 expression, for example, by post-transcriptionally silencing the mRNA that encodes for the synthesis of HMGB1. A suitable method of determining mRNA and miRNA levels is described in more detail below.

In some instances, it may be desirable to screen test agents based on their ability to regulate the activity of HMGB1. As mentioned previously, it has been surprisingly discovered that HMGB1 promotes dendricity and cell body growth in melanocytes. Thus, the change in dendricity and/or cell body growth of a melanocyte may be used as an indicator to determine if a test agent is identified as a skin tone agent. The mechanism of action by which the test agent regulates the activity of HMGB1 is not particularly limited as long as the ability of HMGB1 to promote dendricity in melanocytes is inhibited. For example, the test agent may inhibit HMGB1 from being released by keratinocytes (or other cells); inhibit HMGB1 from binding to or being taken up by the melanocyte (e.g., by competing for or otherwise inactivating molecular binding sites on the melanocyte) and/or render HMGB1 inert.

The ability of a test agent to inhibit dendricity and cell body growth in melanocytes may be determined by contacting a sample of melanocytes with the test agent, measuring the change in dendricity and/or cell body growth and comparing the measured indicator to a control to determine if the test agent is identified as a skin tone agent. In some instances, it is important for the test sample to include a source of HMGB1. For example, an amount of HMGB1 (e.g., recombinant HIS-tagged HMGB1 available from Sigma) may be included in the test sample (e.g., at a final level of 0.1 µg/mL), or the test sample may include another type of cell, which can be stimulated to produce HMGB1. A control may be obtained by measuring the dendricity and/or cell body size of the melanocytes prior to contact with the test agent, measuring the dendricity and/or cell body size of the melanocytes in a control sample and/or from the dendricity and/or cell body size of melanocytes published in scientific literature, if available.

The test agent is identified as a skin tone agent when the measured dendricity and/or cell body size of the melanocyte does not correspond to an "increase in dendricity and/or cell body size," which means that (i) the dendricity and/or cell body size of the test sample did not increase relative to the control; (ii) the dendricity and/or cell body size of the test sample increased, but less than the dendricity and/or cell body size of the control; or (iii) the dendricity and/or cell body size of the test sample increased, but the rate of increase in dendricity and/or cell body size of the test sample was less than the rate of increase in dendricity and/or cell body size of the control. The change in dendricity and/or cell body size of the melanocytes may be determined any time after contact with the test agent (e.g., between 1 and 48 hours, 4 and 36 hours, 6 and 32 hours, 8 and 28 hours, or even between 12 and 24 hours). In some instances, it may be desirable to measure the dendricity and/or cell body size of the melanocytes hourly after contact with the test agent and determine the rate and/or amount of change in dendricity and/or cell body size of the melanocytes based on the measurement at about 24 hours. The dendricity and/or body size of the melanocytes may be measured by capturing an image of one or more melanocytes at different times and analyzing the image(s) using suitable computer software. An example of a suitable imaging system is an INCUCYTE ZOOM brand live cell imaging system (available from Essen Bioscience, Ann Arbor, Mich.), operated according to the manufacturer's instructions. An example of a method of measuring dendricity and/or cell body size of melanocytes is provided below.

In some instances, it may be desirable to determine the ability of a test agent to inhibit dendricity and cell body growth in melanocytes by contacting melanocytes with a test agent and an amount of HMGB1. A test sample may be formed by providing a sample of melanocytes (e.g., 1,000 to 2,000,000 cells/mL or about 200,000), optionally suspended in media, a test agent and an amount of HMGB1 in a suitable container (e.g., 96-well plate). The test agent may added directly to the test sample, or the test agent may be added as a dosing solution as described above (e.g., incorporated into a 1:1000 dilution of cell media). HMGB1 may be added to the test sample before, after or at the same time as the test agent (e.g., HMGB1 may be included in the same dosing solution as the test agent and/or may be included in the cell suspension). The amount of HMGB1 should be sufficient to stimulate dendricity and/or cell body growth in melanocytes. A control sample may be prepared in substantially the same way as the test sample, except without the test agent.

In some instances, it may be desirable to determine the ability of a test agent to inhibit dendricity and/or cell body growth in melanocytes by contacting melanocytes and one or more other cell types with a test agent, before during or after exposure to a stimulus that induces HMGB1 production in the other type of cell. A test sample may be formed by providing a sample of melanocytes and another type of cell (e.g., at between 1,000 to 2,000,000 cells/mL), optionally suspended in media, a test agent and a stimulus (depending on the form of the stimulus) in a suitable container (e.g., 96-well plate). The other types of cells suitable for use herein are not particularly limited as long as they are known to provide HMGB1 expression in response to the applied stimulus (e.g., keratinocytes, fibroblasts and/or macrophages). The stimulus is also not particularly limited, and may take the form of a chemical entity (e.g., inflammation marker, reactive oxygen species, acid or base), energy (e.g., ultraviolet radiation, heat, vibration), or the absence of something (e.g., reduced oxygen or carbon), as long as it is known to induce HMGB1 expression in the selected cell type(s). The stimulus is contacted with the cells in a manner appropriate for the form of the stimulus. The test agent may be added before, during or after the cells are contacted with the stimulus. The test agent may added directly to the test sample, or the test agent may be added as a dosing solution as described above (e.g., incorporated into a 1:1000 dilution of cell media). A control sample may be prepared in substantially the same way as the test sample, except without the test agent.

In some instances, melanocytes that have been previously exposed to HMGB1 increase the dendricity and/or cell body size of the melanocytes may be included in the test sample. In this way, the ability of a test agent to reverse the induced change and/or reduce the rate of change may be evaluated.

The dendricity and/or cell body size of the melanocytes in the test sample and control sample, if used, is measured after contacting the cells with the test agent. The change in dendricity and/or cell body size of the melanocytes may be determined any time after contact with the test agent, as exemplified above. It may be desirable to determine the change in dendricity and/or cell body size of the melanocytes based on a measurement taken about 24 hours after contacting the melanocytes with the test agent. The measured change in dendricity and/or cell body size is compared to the dendricity and/or cell body size of the control to determine if the test agent is identified as a skin tone agent. The test agent is identified as a skin tone agent when the measured dendricity and/or cell body size of the melanocytes does not correspond to an increase in dendricity and/or cell body size.

In some instances, the methods herein may used in a tiered screening assay, in which the present method(s) follows and/or precedes one or more other assays. For example, the present method(s) may follow a higher throughput assay that identifies test agents for further screening, or the present method may precede an assay that further evaluates the suitability of test agents identified as skin tone agents by the present method. For example, a test agent may be identified as a skin tone agent based on its ability to inhibit the expression HMGB1 in a first assay, and then further identified as a skin tone agent based on its ability to inhibit an increase in dendricity and/or cell body size of melanocytes in a second assay. In some instances, the first assay may be selected based on its ability to be used as a relatively high throughput screen, while the second assay is selected to identify actives or combinations of actives that work on different or multiple biological pathways.

Compositions

The method herein can be used to identify skin tone agents for use in compositions intended for the cosmetic treatment, regulation, improvement, and/or prevention of uneven skin tone and/or hyperpigmented spots. These cosmetic compositions are for application to a mammalian skin surface and particularly to human skin. The compositions may be in a wide variety of product forms that include, but are not limited to, solutions, suspensions, lotions, creams, gels, toners, sticks, pencil, sprays, aerosols, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

The cosmetic compositions may include a dermatologically acceptable carrier (which may also be referred to as a "carrier") within which one or more skin tone actives identified by the method here are incorporated to enable the skin tone active(s) and optional other ingredients to be delivered to the skin. The carrier may contain one or more dermatologically acceptable solid, semi-solid or liquid fillers, diluents, solvents, extenders components, materials and the like. The carrier may be solid, semi-solid or liquid. The carrier may be provided in a wide variety of forms. Some non-limiting examples include simple solutions, (aqueous or oil based), emulsions, and solid forms (e.g., gels, sticks, flowable solids, amorphous materials).

The compositions herein include a safe and effective amount of a skin tone agent identified by the method described above, along with one or more optional ingredients. The skin tone agent is included in the composition to improve the appearance of hyperpigmented skin by modulating the expression of HMGB1 and/or directly or indirectly inhibiting the activity of HMGB1. Optional ingredients suitable for use herein include any ingredient known for safe use in cosmetic composition of this type, (e.g., emollients, humectants, vitamins; peptides; and sugar amines, sunscreen actives (or sunscreen agents), ultraviolet light absorbers, colorants, surfactants, film-forming compositions, and rheology modifiers). Some non-limiting examples of suitable optional ingredients for use in the present compositions are disclosed in U.S. Publication No. 2008/0206373, filed by Millikin, et al., on Feb. 28, 2008.

Method of Making Skin Care Compositions

The screening method herein is used to identify one or more skin tone agents, which are then incorporated into a skin care composition. The compositions may be prepared using conventional methods such as are known in the art for making topical skin care compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. It is important that the compositions are prepared to provide suitable stability (physical stability, chemical stability, photostability) and/or delivery of the active materials. This may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

Methods of Treating Skin

Various methods of treatment, application, regulation, or improvement may utilize the aforementioned compositions. The composition may be applied to a target skin surface in need of HMGB1 inhibition. For example, the composition may be applied to a skin surface to treat a skin pigmentation conditions (e.g., hyperpigmented spot or uneven tone). Skin surfaces of the most concern tend to be (but are not limited to) those not typically covered by clothing such as facial skin surfaces, hand and arm skin surfaces, foot and leg skin surfaces, and neck and chest skin surfaces (e.g., décolletage). In particular, identification of the hyperpigmented spot may be on a facial skin surface including the forehead, perioral, chin, periorbital, nose, and/or cheek skin surfaces.

The method may include the step of identifying a skin surface for treatment by the composition. The hyperpigmented spot may be identified by the user or another person such as a dermatologist, cosmetician, or caregiver. Identification may be done by visual inspection of the skin for hyperpigmented spots in need of treatment based on size and/or color. Identification of melanin may be done by commercially available imaging devices such SIAscope® V (available from Astron Clinica, Ltd., UK) or the VISIA® Complexion Analysis system (available from Canfield Scientific, Inc., Fairfield, N.J.). Both devices are capable of collecting images of the skin and identifying chromophores such as melanin. These images can then be used to identify hyperpigmented spots or uneven skin tone.

Many dosing regimens exist for the application of the composition to a skin surface. The composition may be applied at least once a day, twice a day, or on a more frequent daily basis, during a treatment period. When applied twice daily, the first and second applications are separated by at least 1 to about 12 hours. Typically, the composition is applied in the morning and/or in the evening before bed.

The composition may be left on the skin surface for a sufficient contact time and/or repeatedly applied a sufficient number of times to achieve the desired HMGB1 inhibition. In certain embodiments, the contact time is greater than about 1 hour, 2 hours, 6 hours, 8 hours, 12 hours, or 24 hours. The contact time is time from application of the composition until the composition is removed. In certain embodiments, the composition may be removed by rinsing or washing the substrate.

The treatment period is ideally of sufficient time to yield HMGB1 inhibition. The treatment period may be of sufficient time to provide an improvement in the appearance of a hyperpigmented spot, a reduction in melanin, or evening of skin tone. The improvement may be a detectable reduction in size of the hyperpigmented spot, a lightening of the hyperpigmented spot (e.g., lighter in color), or a decrease in the amount of melanin of the hyperpigmented spot. The treatment period may involve a single application or multiple applications. The composition may be applied one or more times daily. In some instances, the composition may be applied at least twice daily. Multiple applications may occur over the course of at least 1 week. In some instances, the treatment period may last more than about 4 weeks or more than about 8 weeks. In some instances, the treatment period may extend over multiple months (i.e., 3-12 months) or multiple years.

The step of applying the composition to the skin surface may be done by localized application. In reference to application of the composition, the terms "localized", "local", and "locally" refer to delivering the composition to the targeted area (such as the hyperpigmented spot) while minimizing delivery to adjacent skin surfaces not requiring treatment. It is recognized that localized application does allow for a reasonable amount of the composition to be applied to areas adjacent the targeted area such as a hyperpigmented spot (i.e., the composition is unlikely to be applied or to remain within the boundary of the hyperpigmented spot without some spreading). The form of the composition or the dermatologically acceptable carrier should be selected to facilitate localized application. While certain embodiments of the present invention contemplate applying a composition locally to a hyperpigmented spot, it will be appreciated that compositions of the present invention can be applied more generally or broadly to one or more facial skin surfaces to reduce the appearance of hyperpigmented spots within those facial skin regions.

Suitable methods may comprise any one or more of the abovementioned steps. One suitable method for inhibiting HMGB1 activation of keratinocytes comprises the step of applying a composition comprising a skin tone agent selected from glycerol monoricinoleate (CAS: 141-08-2), hydroxycinnamic acid (CAS: 7400-08-0), galactomyces ferment filtrate (INCI: Galactomyces Ferment Filtrate; e.g., Pitera®), hydrolyzed *Prunus domestica* extract (INCI: Butylene Glycol, Water, Hydrolyzed *Prunus Domestica*; e.g., Clariju®), derivatives of these and combinations thereof. Another suitable method of inhibiting HMGB1 activation of keratinocytes comprises the step of applying a composition comprising glycerol monoricinoleate, hydroxycinnamic acid, galactomyces ferment filtrate, and/or hydrolyzed *Prunus domestica* extract to a skin surface at least daily for a period of time sufficient to inhibit HMGB1 activation of the keratinocytes.

Test Methods

The following test methods are provided to illustrate certain features and advantages of various embodiments of the invention and should not be construed as limiting the scope thereof. These test methods provide a suitable means for plating, dosing, and harvesting cells for use in the present methods. The test methods also provide a suitable means of isolating and analyzing RNA and protein. The test methods further provide a suitable means of determining melanocyte dendricity and cell body size. While particular cells, materials, and/or equipment may be exemplified in the test methods, it is within the skill of the ordinary artisan to adapt the test methods to use other cell types, materials, and/or containers, which are equivalent to those disclosed herein.

Plating

Make a 210 mL suspension of keratinocytes at 40,000 cells/mL using suitable media to make a cell suspension. Place 2 mL of the cell suspension into the appropriate number of wells of one or more 12-well plates as needed, using the same velocity and insertion angle for each well as cells are pipetted. Incubate the 12-well plates overnight at 37° C. If the cell plating quality is poor (e.g., cells are not attached to plate or seeding density is uneven), discard and start over.

Dose Preparation

Prepare a dosing media by diluting the test agent to the desired concentration (e.g., from 0.0001% to 10%) in a suitable media (e.g., the same media used to make the cell suspension). Diluting the test agent to suitable level (e.g., between 0.0001% and 10%, 0.01% and 8%, 0.1% and 5%, or 0.5% and 3%) can be important when trying to simulate the in vivo effects of the test agent in a skin care composition). It is not uncommon for skin care actives to be included in skin care compositions at these levels. Optionally, include sufficient solublizer to provide 0.1% solublizer in the test sample. Add 2 mL of dosing media into each well of a 12-well plate and incubate at 4° C. overnight or until test agent is to be added to the test sample.

Dosing

Place prepared dosing media in the 37° C. incubator for at least 30 minutes, or until pH has equalized. When dosing media is warmed and at proper pH, dose the cells. Incubate the dosed cells at 37° C. for 6 hours.

Harvesting

In the last 20 minutes of the 6 hour incubation, view every well under a microscope. Take pictures (e.g., micrographs) of every control and every sample exhibiting morphological changes, toxicity, or precipitations. Dump the media from the 12-well plates into a bucket. Pat on paper towels to further remove media. Rest the plates upside down on fresh paper towels for 1-2 minutes, and pat again to remove residual media. Use an 8-channel MATRIX brand pipette (with a tip on every other channel) to add 700 µL TRIzol® brand reagent to each well. Transfer the lysate from each well into a 96-well plate using the 8-channel pipette that only has every other channel loaded. Place a sticky plate cover on the 96-well plate and place for storage at −20° C.

RNA Isolation:

Total RNA (including small RNAs) are isolated from cell lysates using QIAgen® (Helden, Germany) miRNeasy Mini columns according the manufacturer's instructions. Lysates are homogenized by brief vortexing and may be frozen at −80° C. until ready for purification. For purification, lysates are thawed on ice and then extracted once in chloroform. Ethanol is added to the aqueous phase of the extract and this mixture is added to RNeasy® spin columns. The columns are washed to remove contaminants and purified total RNA is eluted from the columns in warm nuclease-free water. RNA quantity is determined using a NanoDrop® 8000 (Thermo Scientific, Waltham, Mass.) spectrophotometer. RNA quality and integrity is confirmed using the Agilent® (Santa Clara, Calif.) 2100 BioAnalyzer. Purified RNA is stored at −80° C.

mRNA Analysis:

250 ng of total RNA is converted to GeneChip® brand microarray targets using the Affymetrix® (Santa Clara, Calif.) HT 3' IVT Express protocol optimized for use on the Beckman Coulter® (Indianapolis, Ind.) Biomek® FXp automation workstation. The labeled target is hybridized overnight to Affymetrix® U219-96 brand microarray plates followed by washing, staining, and scanning on the Affymetrix® GeneTitan® instrument according to the manufacturer's protocol.

miRNA Analysis:

1 ug of total RNA is labeled using the Affymetrix® FlashTag Biotin HSR labeling kit and protocol provided. Biotin-labeled RNA is hybridized overnight to Affymetrix® miRNA 3.0-96 brand microarray plates followed by washing, staining, and scanning on the Affymetrix® GeneTitan® instrument using the provided protocol.

HMGB1 Quantitation from Keratinocytes

Keratinocytes (or other cells) are plated out in 12 well plates as described above with a seeding density of about 200,000 cells/well and incubated overnight at 37° C. with 5% $CO_2$. The keratinocytes are dosed with a dosing medium containing the test agent and the plates returned to the incubator for another 20 hours. The supernatant for each is collected and the HMGB1 level analyzed using ELISA (USCN Life Sciences) in accordance with manufacturer's instructions. The cells are lysed with Glo Lysis Buffer (Promega) and the protein levels determined using BCA kits (Pierce) per manufacturer's instructions. The values of HMGB1 determined by ELISA and normalized to total protein levels from the cells.

Melanocyte Dendricity and Size Measurements

Primary human melanocytes (ATCC) are cultured for 2 passages in T150 flasks. For dendricity experiments, melanocytes are plated into 96 well plates (clear) at a density of about 5000 cells/well. The plates are placed into an Incucyte ZOOM® live cell imaging system (Essen Bioscience, Ann Arbor, Mich.) which resides inside a 37° C., 5% $CO_2$ incubator. 20× images are collected every hour using the phase mode. The Neurite Outgrowth Software Package (Essen) is used to measure cell body size, dendrite length, and cell numbers.

EXAMPLES

Example 1

This example demonstrates the ability of the present method to identify a test agent as a skin tone agent according to its ability to reduce HMGB1 levels. Table 1 below illustrates the change in HMGB1 level as a result of contacting keratinocytes with hydroxycinnamic acid ("HCA") or methyl hydroxycinnamic acid ("ME-HCA") at different concentrations. The control sample is the same as the test sample, except without the test agent. The test samples and control in Table 1 were prepared and analyzed according to the methods herein. As shown in Table 1, HCA and ME-HCA significantly reduced HMGB1 levels relative to the control. Accordingly, HCA and ME-HCA would be identified as skin tone agents according to the present method.

TABLE 1

|  | HMGB1 (pg)/protein (ug) | p-value vs control |
| --- | --- | --- |
| Keratinocyte - vehicle control | 54 |  |
| 0.001% HCA | 29 | 0.087532 |
| 0.005% HCA | 6 | 0.028851 |

TABLE 1-continued

|  | HMGB1 (pg)/protein (ug) | p-value vs control |
|---|---|---|
| 0.02% HCA | 2 | 0.021411 |
| 0.001% ME-HCA | 33 | 0.091905 |
| 0.005% ME-HCA | 28 | 0.043983 |
| 0.02% ME-HCA | 4 | 0.020119 |

Example 2

This example further demonstrates the ability of the present method to identify a test agent as a skin tone agent according to its ability to reduce HMGB1 levels. Table 2 below illustrates the change in HMGB1 level as a result of contacting keratinocytes with galactomyces ferment filtrate ("GFF"), commercially available as Pitera®, or *Prunus domestica* extract ("*Prunus*"), commercially available as Clariju®, at different concentrations. The control samples are the same as the test samples, except without the test agent. The test samples and control in Table 2 were prepared and analyzed according to the methods herein. As shown in Table 2, GFF and *Prunus* significantly reduced HMGB1 levels relative to the control. Accordingly, GFF and *Prunus* would be identified as skin tone agents according to the present method.

TABLE 2

|  | control | GFF (1%) | *Prunus* (0.01%) | *Prunus* (0.03%) |
|---|---|---|---|---|
| replicates (HMGB1/ ug protein) | 66 | 24 | 42 | 23 |
|  | 78 | 14 | 51 | 42 |
|  | 53 | 8 | 39 | 37 |
|  | 61 | 18 | 37 | 31 |
| AVG HMGB1/ ug protein | 64.5 | 16 | 42.25 | 33.25 |
| p-value vs control | 1 | 0.000235552 | 0.010593229 | 0.003314715 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a skin care composition, comprising:
    a) suspending cells in a first medium at a concentration of between about 1,000 cells/mL and about 2,000,000 cells/mL to provide a test suspension;
    b) placing at least some of the test suspension in a container;
    c) contacting at least some of the suspended cells in the container with a test agent to make a test sample;
    d) determining a level of a biomarker present in the test sample, the biomarker comprising high-mobility group protein B1 (HMGB1);
    e) comparing the level of the biomarker of (d) to a control comprising the test suspension cells without the test agent;
    f) identifying the test agent as a skin tone agent when, relative to the control, the level of HMGB1 present in the test sample does not correspond to an increase in HMGB1 level; and
    g) incorporating an effective amount of the skin tone agent into a dermatologically acceptable carrier to form the skin care composition.

2. The method of claim 1, wherein the cells are selected from the group consisting of keratinocytes, fibroblasts, and macrophages.

3. The method of claim 1, wherein at least some of the cells in the test sample are chemically lysed, total protein level of the test sample is determined, and the level of HMGB1 present in the test sample is normalized against the total protein level.

4. The method of claim 1, wherein at least some of the cells in the test sample are chemically lysed and HMGB1 mRNA is isolated, labeled, and hybridized to a microarray.

5. The method of claim 1, wherein the test agent is diluted in a second medium.

6. The method of claim 5, wherein the test agent is diluted to a concentration of from 0.0001% to 10% w/v.

7. The method of claim 1, wherein the control is a cell suspension comprising a same type of cell as the test sample.

8. The method of claim 7, wherein the control includes a solublizer.

9. The method of claim 8, wherein the solublizer is dimethyl sulfoxide.

10. The method of claim 1, further comprising incorporating at least one additional ingredient selected from emollients, humectants, vitamins, peptides, sugar amines, sunscreen actives, ultraviolet light absorbers, colorants, surfactants, film-forming compositions, rheology modifiers, and combinations of these into the composition.

* * * * *